United States Patent
Siddiqui (10) Patent No.: US 9,642,529 B1
(45) Date of Patent: May 9, 2017

(54) PROACTIVE AND PREVENTIVE HEALTH CARE SYSTEM USING REMOTE MONITORING AND NOTIFICATIONS

(71) Applicant: eMobileCare Corporation, Redmond, WA (US)

(72) Inventor: Khalid Umar Siddiqui, Redmond, WA (US)

(73) Assignee: eMobileCare Corporation, Redmond, WA (US)

( * ) Notice: Subject to any disclaimer, the term of this patent is extended or adjusted under 35 U.S.C. 154(b) by 0 days.

(21) Appl. No.: 14/728,110

(22) Filed: Jun. 2, 2015

Related U.S. Application Data (63) Continuation-in-part of application No. 14/210,099, filed on Mar. 13, 2014, now abandoned.

(60) Provisional application No. 61/802,674, filed on Mar. 17, 2013.

(51) Int. Cl.
| | |
|---|---|
| *A61B 5/00* | (2006.01) |
| *A61B 5/024* | (2006.01) |
| *A61B 5/0205* | (2006.01) |
| *A61B 5/1455* | (2006.01) |
| *A61B 5/02* | (2006.01) |

(52) U.S. Cl.
CPC .......... *A61B 5/0008* (2013.01); *A61B 5/0004* (2013.01); *A61B 5/02055* (2013.01); *A61B 5/02433* (2013.01); *A61B 5/02444* (2013.01); *A61B 5/14552* (2013.01); *A61B 5/6802* (2013.01)

(58) Field of Classification Search
None
See application file for complete search history.

(56) References Cited

U.S. PATENT DOCUMENTS

| | | | |
|---|---|---|---|
| 2007/0121959 A1* | 5/2007 | Philipp | H04R 1/1041 381/74 |
| 2012/0083705 A1* | 4/2012 | Yuen | A61B 5/0002 600/508 |

OTHER PUBLICATIONS

Mattoli et al, A Universal Intelligent System-On-Chip Based Sensor Interface, Aug. 17, 2010, Sensors, vol. 10, pp. 7716-7747.*

(Continued)

*Primary Examiner* — Robert Morgan
*Assistant Examiner* — Gregory Lultschik
(74) *Attorney, Agent, or Firm* — Karthik Murthy; Murthy Patent Law PLLC (57) ABSTRACT

A health status monitoring and reporting system comprising a user-wearable armband and a gateway device is disclosed. The armband comprises a power source, a positional sensor and/or a movement sensor, a vital signs measurement device, and a transmitter operated. The vital signs measurement device generates output signals including an indicator of a health condition of the user. The transmitter is configured to receive outputs from the accelerometer and the vital signs measuring device, and transmit signals to an ultra low power network. The gateway device transmits data from the ULP network to a Wide Area Network for processing, data storage, notifications, or the like.

2 Claims, 9 Drawing Sheets

(56) References Cited

OTHER PUBLICATIONS

Kumar et al, Design and Implementation of Portable health Monitoring System Using PSoC Mixed Signal Array Chip, International Journal of Recent Technology and Engineering, vol. 1 Issue 3, Aug. 2012.*

Mackensen et al, Bluetooth Low Energy (BLE) based wireless sensors, Sensors, 2012 IEEE, Oct. 2012, pp. 1-4.*

* cited by examiner

PROACTIVE AND PREVENTIVE HEALTH CARE SYSTEM USING REMOTE MONITORING AND NOTIFICATIONS

CROSS-REFERENCE TO RELATED APPLICATIONS

This is a continuation-in-part of application Ser. No. 14/210,009, filed Mar. 13, 2014, which claims the benefits of U.S. Provisional application No. 61/802,674, filed on Mar. 16, 2013, the entire contents of which are hereby incorporated herein by this reference.

TECHNICAL FIELD

The invention relates generally to the field of health monitoring devices, and more particularly to monitoring the health condition status of a person via instrumentation and communication devices integrated in a patient-wearable structure.

BACKGROUND

The cost of healthcare has been a challenging issue in the United States, with nearly one of every five dollars' worth of the country's gross domestic product (GDP) going to medical expenditures. In an effort to control the cost of healthcare, medical devices and communication technology have been used in combination to monitor chronic diseases and symptoms that could develop into serious conditions.

Various types of patient monitoring systems have been disclosed. For example, U.S. Pat. No. 7,448,996 discloses a patient monitoring system for chronic diseases. U.S. Pat. No. 8,217,795 discloses a system for fall detection and alert. U.S. Pat. No. 7,453,364 discloses a safety device system comprising a wearable alarm device to measure physiological signals and a receiver capable of advising the user to wear the alarm device. U.S. Pat. No. 8,328,718 discloses a wearable appliance monitoring cardiac abnormalities in communication with the one or more wireless nodes.

There are always a need for a device and system with capacity of seamless and non-intrusive monitoring meaningful physiological data, enabling critical situation alert and providing pro-active and preventive healthcare.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present example provides a health status monitoring and reporting system comprising a user-wearable armband and a gateway device. The armband comprises a power source, a positional sensor and/or a movement sensor, a vital signs measurement device, and a transmitter. The vital signs measurement device generates output signals including an indicator of a health condition of the wearable device user. The transmitter is configured to receive outputs from the accelerometer and the vital signs measuring device, and transmit measurement data to a gateway via an ultra low power network (ULPN). The gateway device transmits data from the ULPN to a cloud based portal for processing, data storage, notifications, or the like. The portal analyzes the collected data and displays results on a dashboard. Critical situations and trends are alerted to caregivers and family members of the wearable device user. Graphical reports are generated and allow caregivers to see trends and analyze events leading to an incident. The capture and analysis of data around-the-clock (24×7) forms a basis for proactive and preventive healthcare.

The wearable device automatically outputs an alert if a critical situation is detected. The alert is received by the portal and sent to caregivers and family members. The alert will repeat every predetermined time interval (such as 5 minutes) until the alert is cancelled. The cloud-based data is auto-analyzed at a frequent interval, looking for deviation from the norm. If a deviation is found, an alert is raised. A caregiver, such as a family doctor, may be notified, to facilitate in providing proactive and preventive care. This may also indicate a need to change or modify dosage of prescribed medicines.

By remotely monitoring and storing physiological data and providing alerts and notifications, caregivers or family members of wearable device user may view the current and historical data as a dashboard on their mobile devices at anytime from anywhere.

The captured data may also be used like the 'black box' in an aircraft. In case of an incident, a caregiver and a doctor look back in time via the data to see what happened a few hours, a day, a week or a month before the incident, and draw conclusions. With the right data, tools, and studies, this will have a huge impact on the quality of healthcare and will result in cost savings.

One embodiment of the invention relates to a solution to capture physiological and environmental data. Physiological data includes vital signs, body movement patterns, activity states and duration of each activity. Environmental data includes sensors to detect opening and closing of doors, ambient light and temperature, gas or water leaks, sound, motion, to read Near Field Communications (NFC) tags or Radio Frequency Identification (RFID) tags. Such data help in forming a complete picture of a user's status, environment, and activities, for making informed decisions for healthcare and safety.

Various sensors and technologies are used to seamlessly gather physiological data by using an unobtrusive arm band. A remote monitoring service is alerted if a critical situation is detected, or if the device is taken off, or if it fails self-diagnostics. The device uses algorithms configured to enable ultra-low power consumption for collecting and sending data. Collected data is analyzed to provide proactive and preventive healthcare.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The examples below describe a health status monitoring and reporting system. Although the present examples are described and illustrated herein as being implemented in a local health status monitoring device and a network reporting implementation, the system described is provided as an example and not a limitation. As those skilled in the art will appreciate, the present examples are suitable for application in a variety of different types of monitoring and reporting systems.

The embodiments depicted in the several drawing figures have several hardware and software components, as are described in detail in the following paragraphs. For convenient reference, the numeric labels in the drawing figures correspond to the following features:

Drawing - Reference Numerals

| 100 | Wearable Device (WD) | 102 | Ultra-Low Power (ULP) Network using Bluetooth 4.0 or Zigbee IEEE 802.15.4 |
| --- | --- | --- | --- |
| 104 | Environmental sensors like door open, gas detected, water, temperature etc. | 106 | Gateway device to connect ULP network to Wide Area Network (WAN) |
| 108 | Cellular radio/transceiver | 110 | WI-FI transceiver |
| 112 | Cloud based services | 114 | Web Portal for dashboard and data |
| 116 | Database in the cloud | 118 | user devices |
| 200 | Rechargeable 3.3 volt battery | 202 | Accelerometer MEMS chip |
| 204 | Reflectance Heart Rate Monitor/Oximeter MEMS chip | 206 | Pressure Sensor/Altimeter MEMS chip |
| 208 | Gyroscope MEMS chip | 210 | Infrared Temperature sensor chip |
| 211 | Proximity Sensor (Capacitive) | | |
| 212 | Memory with Self-Diagnostics logic | 214 | System on Chip with ULP transceiver |
| 216 | Near-Field Communication (NFC)/Radio-frequency identification (RFID) Tag | 500 | gateway transceiver |
| 502 | Microphone/Speaker | 504 | camcorder |
| 506 | 2-Way Communication | 508 | Wide Area Network |

-continued

Drawing - Reference Numerals

| | Hub | | Interface |
| --- | --- | --- | --- |
| 510 | Cellular transceiver | 512 | Wi-Fi transceiver |
| 514 | Gateway Power Supply | 516 | Buttons to clear Alarm & Reminders |
| 518 | NFC/RFID Reader | 520 | GPS (Optional) |
| 522 | LCD Screen (Optional) | 530 | Gateway processor |
| 600 | Admin task software module | 602 | Security and Compression module |
| 604 | Network Provider module | 606 | Alarm/ Reminder provider |
| 608 | Cloud data provider | 610 | Watchdog provider |
| 612 | Database SQL Lite | 614 | Content Provider |
| 616 | Self & Network diagnostics | 618 | Simulated Data UI |
| 620 | Device Data provider | 700 | API's for data transfer |
| 702 | Database engine at the portal | 704 | Admin Tasks at the portal |
| 706 | Reminders engine | 708 | Reports engine |
| 710 | Portal Dashboard | 712 | E-Mail engine |
| 714 | SMS Text message engine | 716 | Care Giver mobile devices |

Figure 1:
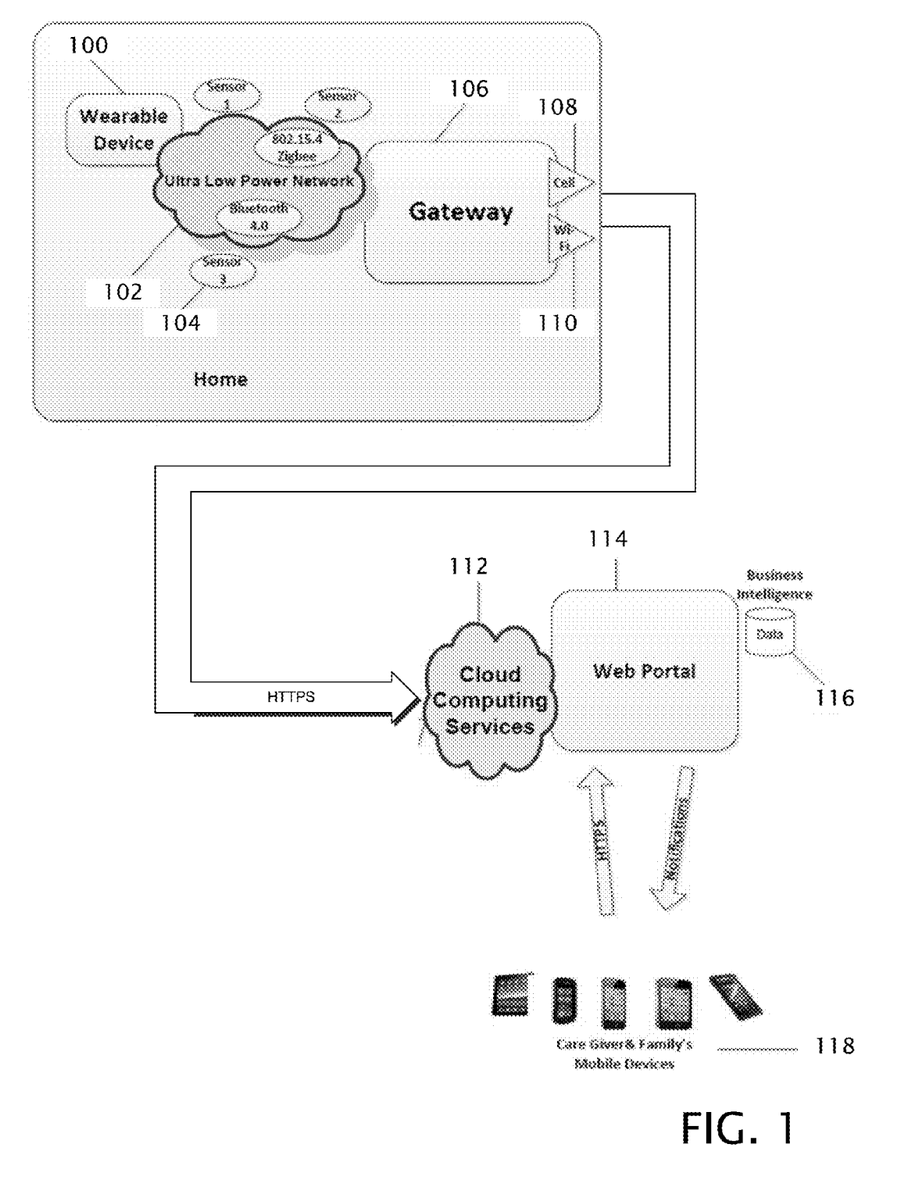
FIG. 1 is an exemplary system diagram showing a health status monitoring and reporting system comprising a wearable device.

FIG. 1 shows an exemplary system diagram showing a health status monitoring and reporting system comprising a wearable device for a device user, according to an exemplary, non-exclusive embodiment. The system comprises a wearable device 100, an ultra low power network 102, a gateway 106, a computing device 112 and a web portal 114 accessible by a plurality of devices of other system users, such as the caregiver and family members of the wearable device user. In one embodiment, the wearable device (WD) 100 is an arm band with various sensors and electronics to capture and transmit useful data. The data are transmitted via the Ultra-Low Power Network (ULTPN) 102. In one embodiment, the ULTPN is based on two low power protocols; Bluetooth 4.0 (Low Energy) and IEEE 802.15.4 (based on the Zigbee communication protocols and specification, for example). The ULPTN is modularly designed to allow use of either of the protocols, or a mix of both, for different sensors. For example, the WD provides good results with Bluetooth 4.0, and environmental sensors work better with Zigbee. In another embodiment, an ANT protocol is used, which is similar to Bluetooth 4.0.

The Gateway 106 is coupled to the ULTPN 102 with built-in transceivers for Bluetooth 4.0 and 802.15.4 protocol-based networks. In one embodiment, the system also comprises at least one environmental sensor 104 coupled to the gateway 106 via one or the other of the ULTPN protocols. In one embodiment, the gateway 106 connects to the internet in order to access a Cloud Computing Services 112, using a wide area network interface such as a cellular radio 108. In one embodiment, the cellular is a 3G, CDMA or 3GPP, or 4G LTE network. In another embodiment, the gateway 106 connects to the internet by using a built-in Wi-Fi interface 110. This method may only be used if a Wi-Fi router is available and functional at the place where the wearable device user will be monitored; e.g., at the place of residence. Sending data over Wi-Fi is cost effective. A built-in, device-executable instruction set embodies an algorithm configured to prefer sending data to the web service via Wi-Fi, if and when available.

In one embodiment, the connection to the Cloud Computing services is encrypted and compressed using HTTPS and JSON protocols. The Web Portal 114 and associated Database 116 are hosted by a cloud service provider known as 'Platform as a Service' (PaaS), such as Amazon Web Service (AWS), Windows Azure or Google App Engine. In all cases, an associated Database engine 116 is used to store persistent data.

The Web Portal 114 is accessible to registered caregivers and/or family member of the wearable device user in a graphical and/or text format. The caregivers and family members may use various user devices 118 to monitor the current situation, as well as to receive alerts via SMS and e-mail notifications. The user device 118 may be a desktop computer or a mobile device, such as a smart phone, a tablet a personal laptop, etc. The only requirement is that the user device should have data and text access to the internet.

Figure 2A:
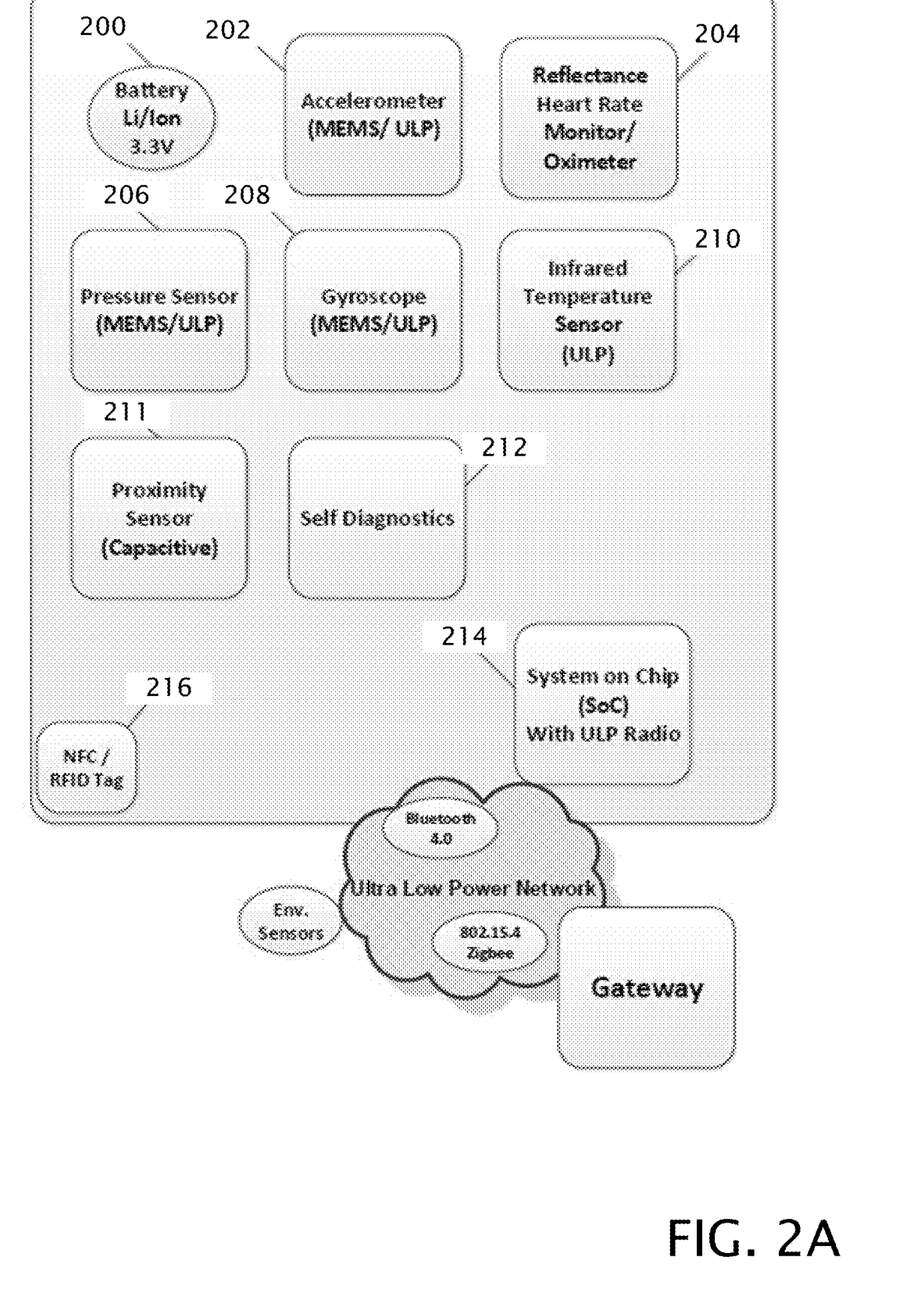
FIG. 2A is an exemplary component diagram of the wearable device.
Figure 2B:
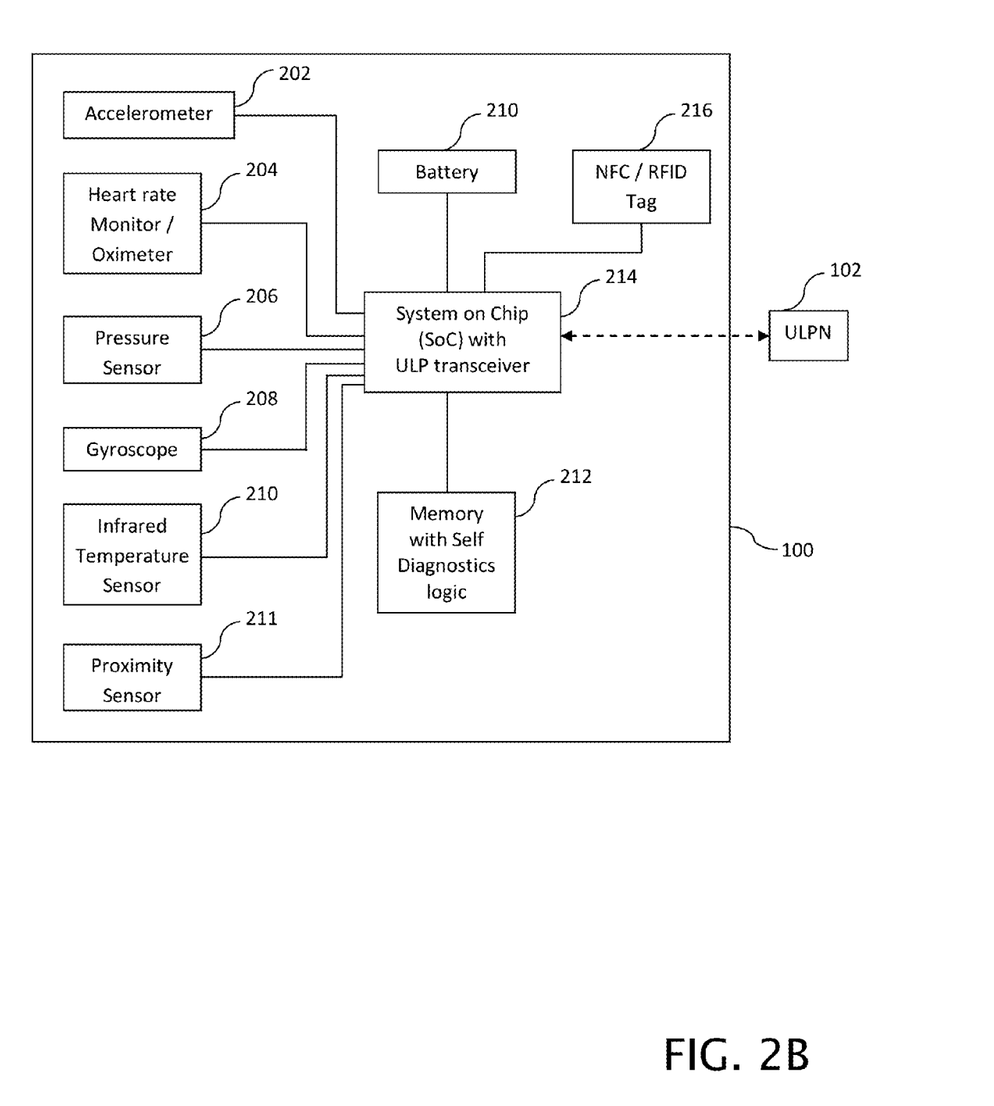
FIG. 2B is an exemplary schematic diagram of the wearable device.

FIG. 2A shows an exemplary component diagram of the wearable device and FIG. 2B shows an exemplary schematic diagram of the wearable device. In one embodiment, the wearable device (WD) is a watch size band attached to an upper arm of a user. The wearable device (WD) may also be other wearable configurations, such as a belt, a wrist band, or the like. In a preferred embodiment, the wearable device is non-intrusive with no sensor actually touching the body such that a user is likely to forget that it is even being worn. The wearable device comprises a batter 200, an accelerometer 202, a heart rate monitor (oximeter) 204, a pressure sensor 206, a gyroscope 208, an infrared temperature sensor 210, a proximity sensor 211, a memory loaded with self diagnostic 212, a system on chip (SoC) 214 and a NFC/RFID tag 216. The System-on-Chip (SoC) 214 receives inputs from all the aforementioned sensors and transmits outputs to the ULPN 102.

The memory 212 is integrated within the SoC chip or a separate memory IC. The memory is a storage loaded with self-diagnostics logic and any other software (or firmware) instructions (or algorithm) executable by the device for the operation of the wearable device. In one embodiment, the memory 212 also comprises a buffer for temporarily storing data from outputs of various sensors.

The gyroscope 208 functions as a position sensor and the accelerometer 202 functions as a movement sensor. The accelerometer sensor is designed to measure the acceleration and tilt. The gyroscopic sensor measures the angular velocity and orientation. Gyroscope and accelerometer has been used, individually or in combination, in initial navigation to determine acceleration, position, orientation, speed, etc.

The heart rate monitor (oximeter) 204 may be a reflectance heart rate monitor, a reflectance oximeter or a combination of both. The heart rate monitor (oximeter) 204, and the infrared temperature sensor 210 are examples of a vital signs measurement sensor, and are not intended to represent the only forms in which the present example may be constructed or utilized. The wearable device may also comprises or incorporate other vital signs measurement sensors, for other vital signs measurements.

The System-on-Chip (SoC) 214 is a microprocessor based system with all the necessary components (including the microprocessor) combined on a single chip, including an ultra-low power transceiver (comprising both a transmitter and a receiver) for connection to the gateway. In one embodiment the SoC is a Texas Instruments CC2541 device, which has a built-in Bluetooth 4.0 transceiver. In another embodiment, the SoC is an Atmel ATMEGA128RFA1 device, which has a built-in Zigbee transceiver. In yet another embodiment, the SoC is a Nordic nRF51 822 device, which has a built-in Bluetooth 4.0 transceiver. In an embodiment, an I2C bus and an SPI bus are used to connect sensors to the SoC, as all sensors have either a I2C bus or SPI bus connection capabilities. In an embodiment, the Reflectance Heart Rate Monitor/Oximeter 204 is connected to an internal analog-to-digital converter (ADC) of the SoC. In still another embodiment, the analog-to-digital conversion is performed on the subassembly, and only the result is fed into the SoC.

The power for the operation of the wearable device (the SoC 214 and any other applicable sensors requiring power input) is supplied by the battery 200. In one embodiment, the battery is a 3.3 volts Lithium Ion rechargeable battery, although other battery technologies that likewise provide a suitable voltage are also contemplated within the embodiments. In a preferred embodiment, the WD 200 is water proof and consumes an ultra-low amount of power; therefore the battery is expected to last a long time, up to several months or even a year between charges. In some embodiment, the WD 200 may even comprises a motion charger using kinetic energy from wearable device movement to charger the battery for even longer time of battery life.

Figure 3:
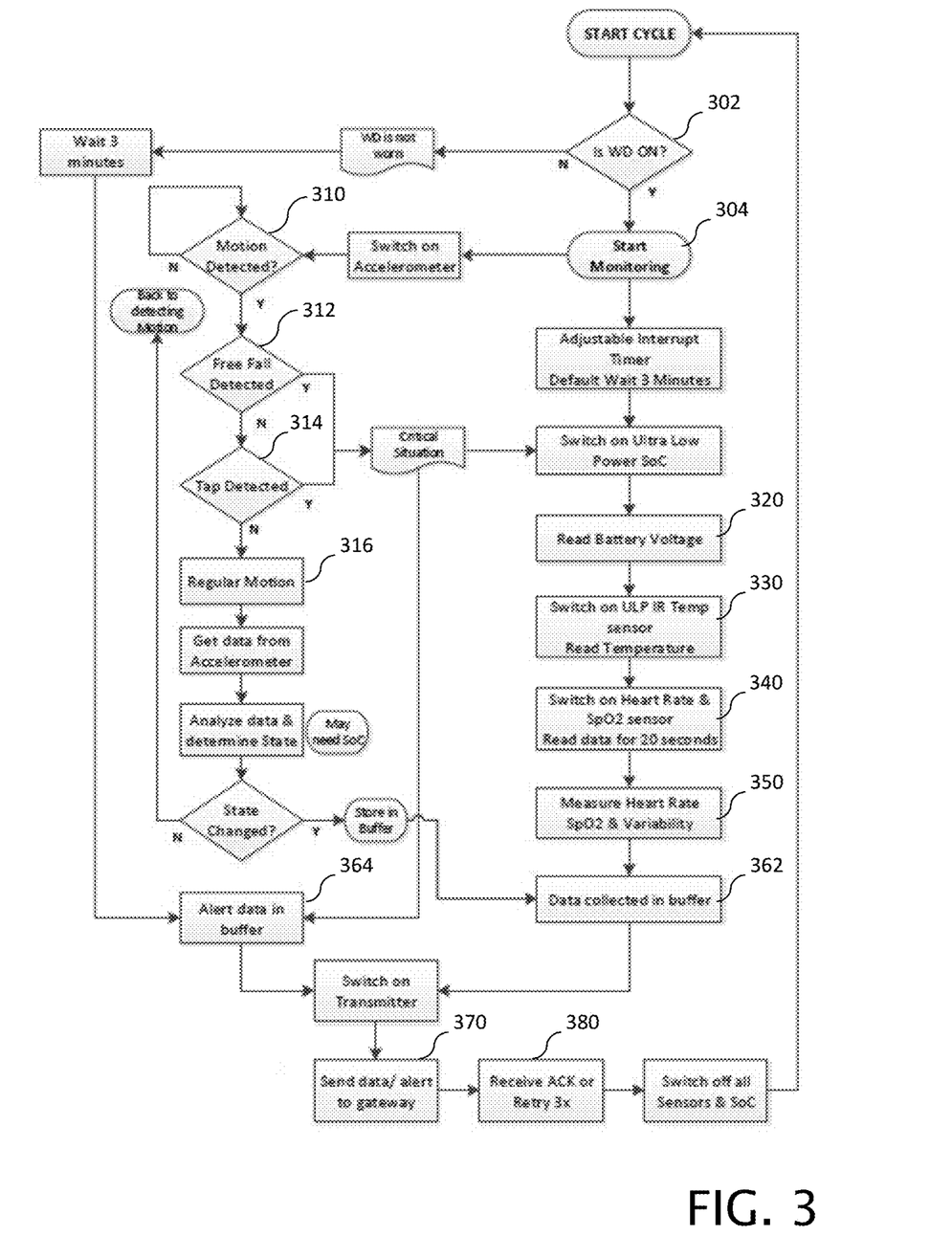
FIG. 3 is an exemplary process flow diagram of the wearable device.

FIG. 3 is an exemplary process flow diagram of the wearable device when the algorithm within the memory 212 is executed by the microprocessor within the SoC 214.

At step 302, WD being worn is verified. If the WD 100 is not being worn, an alert is generated and the alert data is stored in the buffer. The monitoring cycle is terminated (as shown in FIG. 3) to save power. The SoC and all sensors (except the accelerometer) are either off or in sleep mode either for a predetermined time, such as 3 minutes, or until user wearing is detected. In one embodiment, user wearing may be checked by measuring two parameters. A first parameter is from the heart rate monitor 214. If no heart beat is detected, the device is likely to be off the arm (not being worn). A second parameter is from the temperature sensor 210, which should within a reasonable range of human temperature range. With the combination of these two parameters, a decision could be made whether or not the device is being worn. The status is then sent to the gateway for further processing. Alternatively, the status is checked by the capacitive proximity detector 211. The optical sensor may also be used for proximity detection. If the device is not being worn, the measurement cycle would terminate at the start to conserve battery power.

After the wearable device is detected to be worn by the device user, the device starts vital signs and other measurements in step 304. In step 310, the device user's body motion is detected, using an ultra-low power Accelerometer 202 on a Micro-Electromechanical System (MEMS) chip. In an exemplary embodiment, the accelerometer chip is an Analog Devices ADXL362 device, and the Gyroscope 208 is an InvenSense IMU 3000 device. In another exemplary embodiment, an InvenSense MPU9250 chip combines each of an accelerometer 202, a gyroscope 208, and a pressure/altitude sensor 206 in a single MEMS chip. In step 330, the device user's body temperature is measured with the temperature sensor 210. In step 350, the device user's heartbeat rate and/or SpO2 is measured after the Heart rate Monitor/Oximeter 204 is switched on in step 340 with measurement for a predetermined measurement interval, such as 20 seconds, for stable and reliable data reading.

In a preferred embodiment, the ultra-low power accelerometer is on at all times and generates interrupts in case of a critical situation like a fall in step 312 or a tap in step 314. Tapping on the device, which is detected by the accelerometer, may indicate a request for help in the manner of a 'panic button.'

Detection of a critical situation by the accelerometer interrupts wakes up a Microprocessor unit (MCU) in the SoC to perform further analysis, and to send the data and an alert to the gateway 106 using the ultra-low power network. The accelerometer also detects normal motion in step 316 and categorizes the type of motion, and sends the data to the gateway. In one embodiment, the SoC and the sensors are woken up to obtain readings of vital signs, even if there is no motion detected, every a predetermined interval, such as 5 minutes. The predetermined interval may be programmable. Self-diagnostics, such as reading a battery voltage level in step 320 and user wearing check, are performed during the woken-up period and the self-diagnostics results are sent to the gateway.

In step 362, the sensor measurement data are collected and stored in the buffer within the memory 212. In step 364, alert data recorded under critical situations are also collected and stored in the buffer within the memory 212. In step 370, all the measurement data and alert data are sent to the gateway 106 using the transceiver within the SoC 214. In step 380, the WD 100 receives an acknowledgement from the gateway or try to send the data three times if no acknowledgement received.

Those skilled in the art will realize that the process sequences described above may be equivalently performed in any order to achieve a desired result. Also, sub-processes may typically be omitted as desired without taking away from the overall functionality of the processes described above.

In exemplary embodiments, the Digital Infrared temperature sensor 210 comprises a Texas Instruments TMP006 210 device, and the Pressure/Altitude sensor is a Freescale MPL3115A2 206 device. The Reflectance Heart Rate Monitor/Oximeter 204 is a subassembly containing an Infrared LED, a red LED, a photo sensor, and a Texas Instruments AFE4490 analog front end device with operational amplifiers and filters, to obtain heart rate and oxygen saturation level by measuring the light reflected by the user's arm. Such configuration makes the WD non-intrusive and safe, with none of the sensors actually touching the skin.

The WD typically includes an NFC/RFID tag for identification, which is read by an environmental sensor 104 for tracking and also for identification to the gateway. The WD is authenticated and paired to the gateway by bringing it to within a close proximity to the gateway using the transceiver within the SoC 214.

In one embodiment, the WD 100 also supports upgrade of firmware 'over the air' through the transceiver within the SoC 214. The firmware upgrade may be initiated by the gateway 106 and/or cloud computing service 112.

Figure 4:
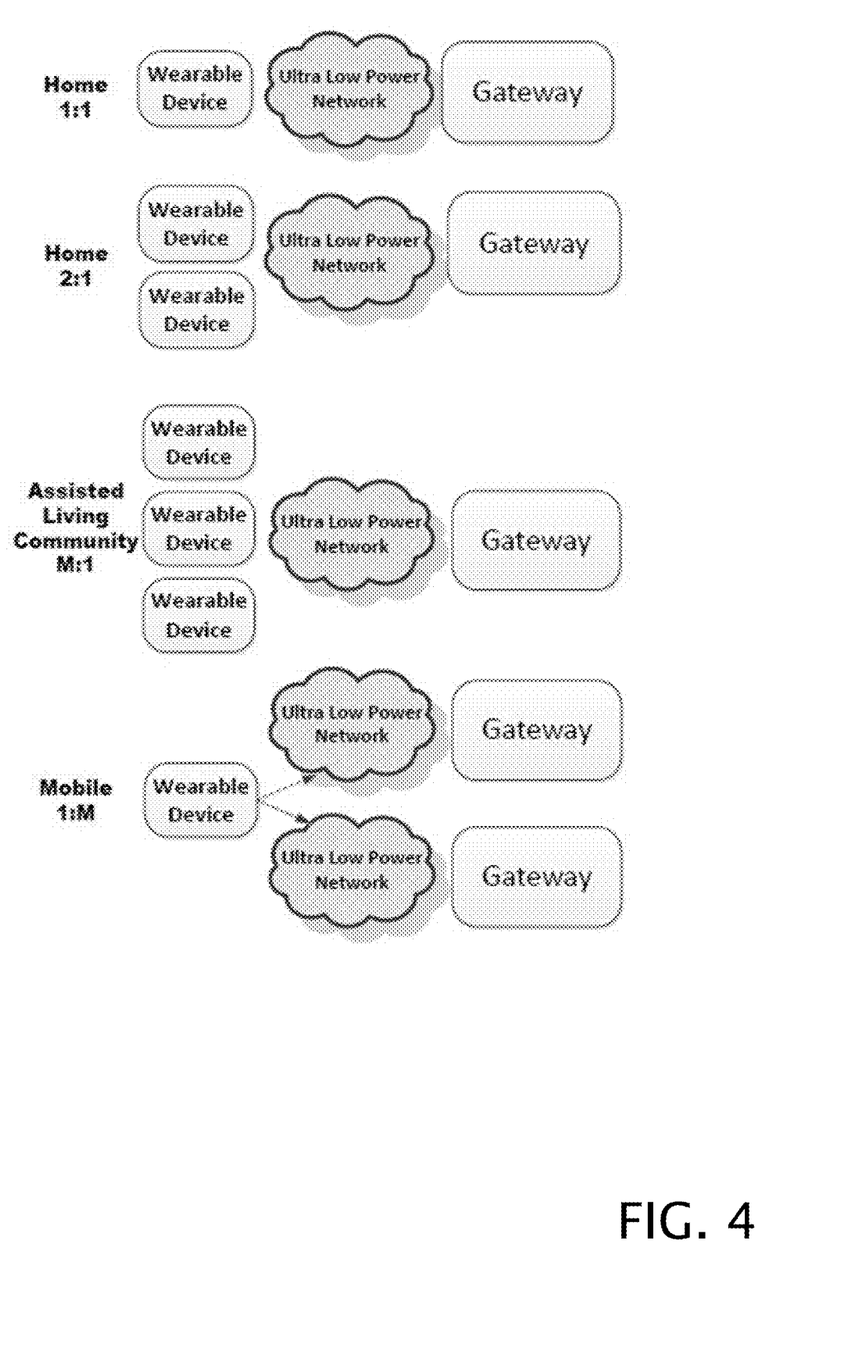
FIG. 4 shows various configurations and types of the connections between the wearable device and the gateway.
Figure 5A:
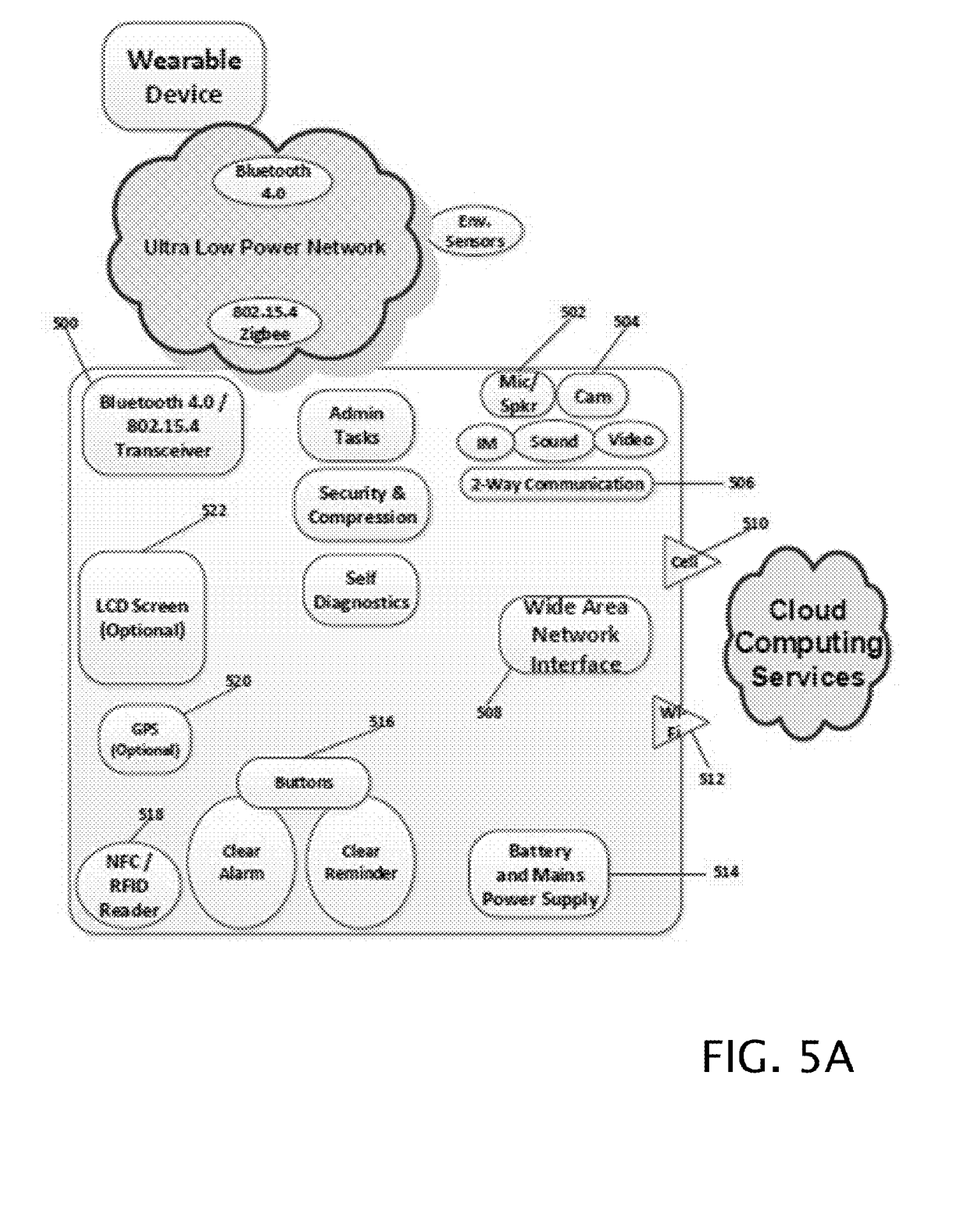
FIG. 5A is an exemplary component diagram of the gateway.
Figure 5B:
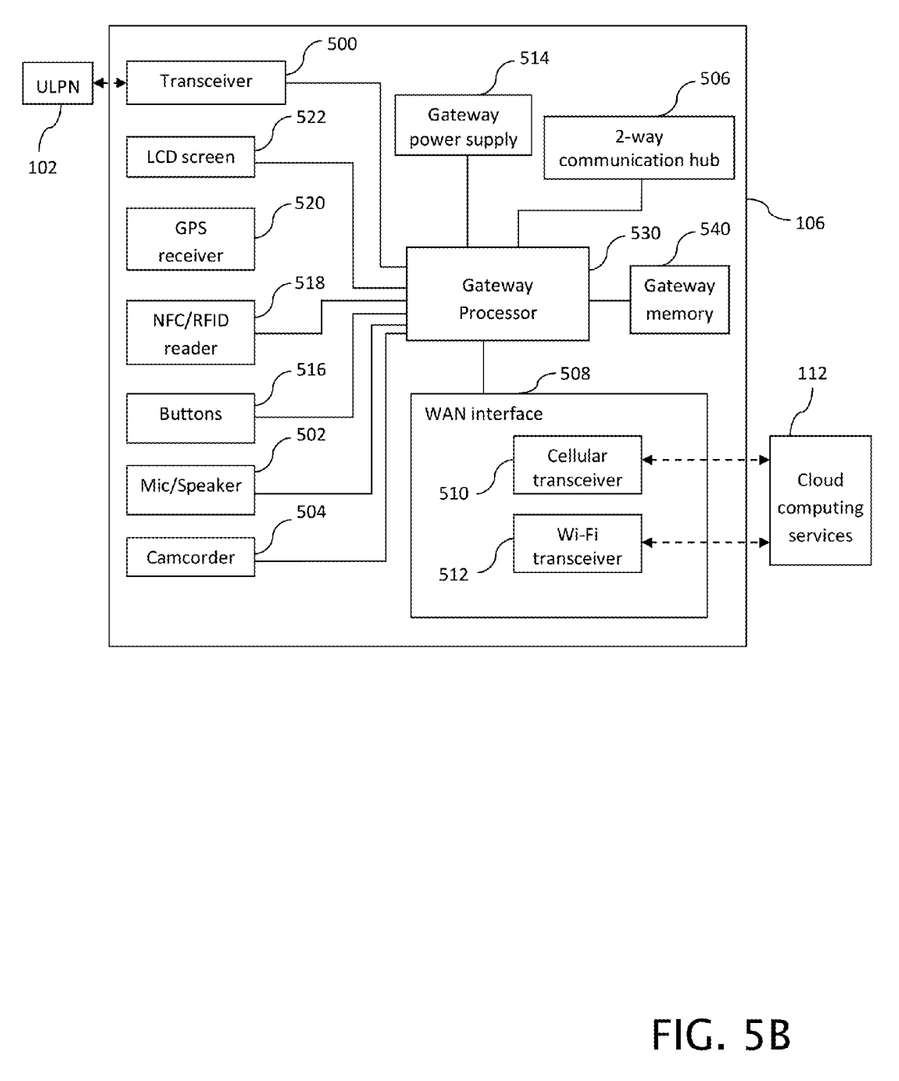
FIG. 5B is an exemplary schematic diagram of the gateway.

FIG. 4 shows various configurations and types of the connections between the wearable device and the gateway in different situations. A 1:1 (one-to-one) connection is for a single wearable device user. A 2:1 (two-to-one) connection is for two wearable device users who may live together at home. A single gateway is shared between the two devices. In a preferred embodiment, every fragment of data sent by each WD has a device ID in the header, enabling the gateway 106 to establish the source of the data. A M:1 (many-to-one), or multiple WD to one gateway, is an extension of the 2:1 connection and works on the same principal. This scenario applies to assisted living and retirement home communities. A 1:M (one-to-many) is when the user is mobile and moves from one gateway to another gateway. Examples include, a WD user moving from a room to a community gathering area within an assisted living or retirement home, or one WD user visiting another WD user. The common theme is that a WD user can utilize any allowed gateway, using the gateway as a data conduit to the cloud computing service 112. However, downstream services like a medicine reminder and two-way communication may only work with the assigned gateway FIG. 5A shows an exemplary component diagram of the gateway and FIG. 5B shows an exemplary schematic diagram of the gateway. The gateway 106 comprises electronics hardware and software logic that communicate to the ultra-low power network and the Cloud Computing Services 112. In essence, the gateway 106 is a hub of the ultra-low power network 102. In one embodiment, the gateway 106 may comprise a gateway transceiver 500, a Mic/speaker 502, a camcorder 504, a 2-way communication hub 506, a WAN (wide area network) interface 508, a plurality of buttons 516, a NFC/RFID reader 518 to identify wearable device identification, a GPS receiver 520, a LCD screen 522, a gateway memory 540 and a gateway processor 530 coupled to the aforementioned gateway components. The gateway memory 540 is a storage loaded with software (or firmware) algorithm executable by the gateway processor 530 for implementation of the algorithm. Power to the gateway is supplied by a gateway power supply 514, which may be a combination of a rechargeable battery and an external mains charger to keep the battery charged while plugged into AC power. The buttons 516, may be hardware and software buttons, allow a user to clear reminders and alarms, which are programmably set according to user preferences.

In one embodiment, the gateway transceiver 500 is a Bluetooth 4.0 and/or 802.15.4 Transceivers to communicate to the ULPN 102. The WAN interface 508 may comprises a cellular transceiver 510 and a Wi-Fi transceiver 512. The WAN interface 508 couples to the cloud computing server 112 using the Cellular transceiver 510 and/or Wi-Fi transceiver 512. The Wide Area Network Interface 508 comprises software codes to maintain and prioritize connection to wide area network.

In one embodiment, the gateway allows 2-way communications with the authenticated caregivers via a 2-way communication hub 506. The camcorder 504, the microphone/speaker 502 and the LCD screen 522 may be integrated within the gateway for video recording, voice input/output, etc, to facilitate communications. The gateway 530 may be fixed or portable. The optional GPS module 520 may be integrated within the gateway for tracking the exact location of the gateway, if the gateway is portable.

In one embodiment, the gateway 106 further comprises modules for administration tasks, to provide security, authentication and data compression. The self-diagnostics module monitors and reports hardware, software and networking issues. The gateway may be a modified tablet computing device (e.g., based on the GOOGLE ANDROID operating system, or an APPLE IPAD device) with a custom application/software (e.g., an "App"). In another embodiment, the gateway is constructed with custom hardware and custom software.

Figure 6:
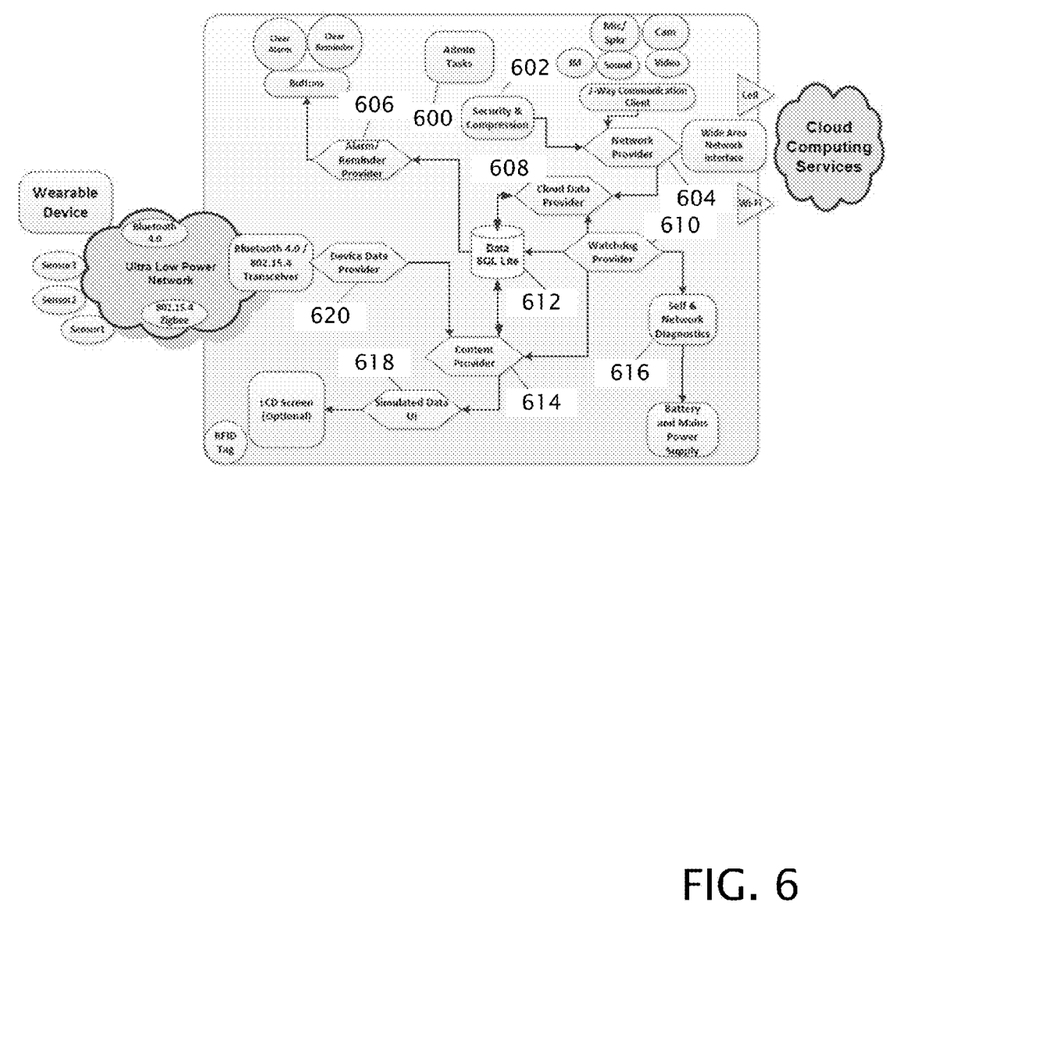
FIG. 6 is an embodiment of the software components, functions, and relationships of the gateway.

FIG. 6 shows an embodiment of the software components, functions, and relationships of the gateway. The administration tasks module 600 supervises the operation of the gateway on an administration level. The Security and Compression module 602 provides communication authentication (device-to-gateway, portal-to-gateway, and users-to-gateway), authorization, and data compression. The Security and Compression module 602 works closely with a Network Provider module 604, which interacts with the Wide Area Network Interface 508 to facilitate data flow and formatting while maintaining security. The network Provider 604 may communicate with a two-way communication client (e.g., a SKYPE client), and also exchange data with the Cloud Data provider 608.

The data is persisted in a SQL Lite database 612, which is stored within the gateway memory 540. Device Data provider 620 collects data from the WD 100 and other environmental sensors 104, and passes the data to a Content provider 614, which stores the data in the SQL Lite database 612. A watchdog provider 610 is a background service that monitors data flow and persistence. Data (sensor measurement and alert data) stored in the database will be deleted after successful transferring to the cloud computing services. A simulated data UI 618 is optional for testing, and displaying data transfer process. A network & self diagnostics module 616 provides diagnostics algorithm for battery, hardware, and network traffic, and alerts sending when necessary. An alarms and reminder provider 606 provides visual and sound notification for alarm and reminder information. The notification may be cleared by the user by pressing a hardware or software button 516. The action of the button 516 is also recorded and sent to the cloud computing services.

In one embodiment, the gateway is plug-and-play; it needs to be plugged in to AC power and switched on. At the first use, the WD 100 is authenticated and paired to the gateway using of NFC/RFID tag. The gateway is typically pre-configured to auto-connect to the WD and environmental sensors, and also establish connection to a Cloud Computing Services Portal. Optionally, the gateway may be connected to a Wi-Fi router, if a router is available. If a critical situation is detected, or is indicated by a tap, the gateway will beep and a 'Clear Alarm' button will flash. User may cancel the alert by pressing or touching the Clear Alarm button on the gateway. If a reminder is set at the portal, for example, to take medicine, the gateway will beep and announce the reminder. The user may cancel the reminder by pressing or touching a 'Clear Reminder' button. Alternatively, the reminder alerts will auto-stop in 30 seconds (or upon the expiration of some other predetermined time duration).

Figure 7:
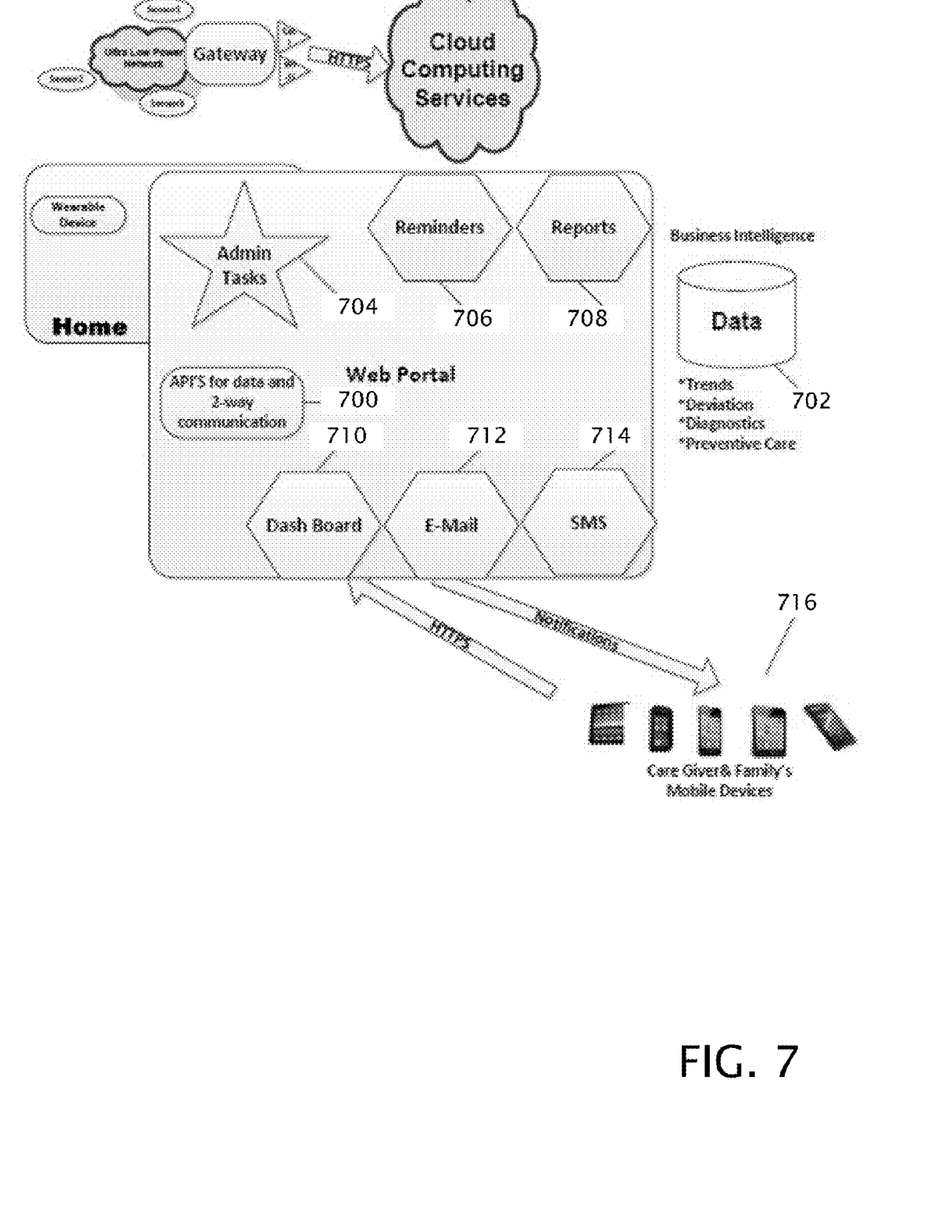
FIG. 7 is an exemplary component diagram of a cloud computing services portal to illustrate various components and services.

FIG. 7 is an exemplary diagram to illustrate various components and services of a cloud computing services (or web portal). In an exemplary embodiment, the web portal (same as the web portal 114 in FIG. 1) is built using Django 1.4 and Python utilities hosted on Apache 2 at Amazon Web Services. A set of Application Programming Interfaces (API) 700 allows data transfer to and from the gateway and allows the two-way communication. The database service is provided by Amazon Relational Data Service (RDS) in the cloud, in an embodiment, based on MySQL database engine 702.

A business intelligence type process is run every three hours (or at some other predetermined time interval) to analyze trends, patterns, and deviations from normal conditions, enabling the provision of proactive and preventive care. An Administration task 704 is provided by an admin console, allowing tasks such as creating users, groups, and access levels. The database engine 702 stores user identification, login credentials, WD data, sensor data, user profiles, data access permissions, notifications, alerts, reminders, etc. at a non-transitory data storage medium, which is accessible and editable by admin users.

Reminders engine 706 gathers and transfer to the gateway the data associated with the wearable device user. Reports engine 708 gathers physiological and sensor data per wearable device user and provides graphical reports to a dashboard 710, which is the primary interface to caregivers and family associated with a wearable device user after authentication. Caregivers and family members may connect to the web portal from their mobile devices 716 at anytime and from anywhere via internet connection. In one embodiment, the mobile devices 716, such as IPHONE, IPAD, WINDOWS phone, ANDROID phone and tablet, are loaded with a customer app for better experience. In one embodiment, users can use a web browser to access the web portal. Text Notifications may be sent by SMS engine 714 using an SMS texting application (e.g., as is available from TWILLIO, etc.). E-Mail notifications may also be sent by an E-Mail engine 212 using SMTP as provided by AWS.

The customer application enables a user to view the current status, and run and view graphical reports regarding to a WD user after authentication checkup. If no critical situation or fault condition presents, the status is all green. In case an alert is generated, the corresponding status icon will turn red and the caregiver or family member will receive an SMS text, and/or an e-mail message. In an embodiment, the text and e-mail are still sent to the caregiver or family member, even though they are not connected to the portal when the alert is generated. The caregiver or family member can also clear the alert from the portal. The caregiver or family member may also set a recurring or one-time reminder from the portal.

In one embodiment, a caregiver or a family member may be tied to more than one wearable device user to view the dashboards of all the wearable device users they are authorized to view.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that embodiments of the methods and system of the invention may be implemented by a computer or microprocessor process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

The invention claimed is:

1. A health status monitoring and reporting system, comprising:
   a. a patient-wearable monitoring device, comprising:
      I. a water proof wearable device band, attached to an upper arm of a user;
      II. a power source, such that the power source only needs to be recharged after several weeks;
      III. a vital signs measurement sensor, which is both a reflectance heart rate monitor and a reflectance oximeter;

IV. wherein the vital signs measurement sensor comprises an Infrared LED, a red LED, a photo sensor, and an analog front end device with operational amplifiers and filters, to obtain heart rate and oxygen saturation level by measuring the light reflected by the user's upper arm, with none of the sensors actually touching the skin;

V. a positional sensor, a movement sensor, a pressure sensor, and a digital infrared temperature sensor;

VI. wherein the movement sensor is a type of accelerometer;

VII. a capacitive proximity detector to determine if the wearable device is being worn;

VIII. an NFC/RFID tag for identification of the wearable device;

IX. a system-on-chip microprocessor coupled to the vital signs measurement sensor and at least one sensor by either or both of a I2C bus and an SPI bus; and X. a transmitter coupled with the power source and configured to transmit from the wearable device to an ultra-low power network (ULPN) data received from one or more of the vital signs measurement sensor, the positional sensor, the movement sensor and the pressure sensor;

XI. the transmitter further configured to communicate with the ULPN via either or both of low energy Bluetooth and IEEE 802.15.4 communication protocols;

XII. the transmitter further configured as a wireless signal transceiver and integrated with the system-on-chip microprocessor;

b. a gateway device coupled to the ULPN to transmit the data from the ULPN to a Wide Area Network (WAN);
  I. the gateway device configured to transmit the data to the WAN via at least one of cellular and Wi-Fi communication technologies;

c. wherein the movement sensor detects critical situations, and if so detected, generates an interrupt to wakeup the System-on-Chip microprocessor to perform further analysis, and to send the data and an alert to the gateway device using the ultra-low power network;

d. the critical situations that the movement sensor can detect consist of the user tapping on the wearable device, which indicates a request for help in the manner of a panic button;

e. the movement sensor also detects motion;

f. the movement sensor is the only part of the wearable device that is always on, and can conserve power by being the only part of the wearable device that is on;

g. wherein environmental sensors
  I. detect opening and closing of doors,
  II. detect ambient light and temperature,
  III. detect sound,
  IV. detect motion,
  V. read Near Field Communications (NFC) tags for identification of the user of the patient-wearable monitoring device and tracking the location of the user of the patient-wearable monitoring device, and
  VI. read Radio Frequency Identification (RFID) tags for identification of the user of the patient-wearable monitoring device and tracking the location of the user of the patient-wearable monitoring device;

h. wherein a non-transitory data storage medium stores data including a unique identification corresponding to the patient-wearable monitoring device;

i. wherein the gateway device transmits data from the ULPN to a cloud based portal for processing, data storage, or notifications;

j. wherein the cloud based portal analyzes the collected data and displays results on a dashboard;

k. wherein a cloud based portal is accessible to registered caregivers and family members of the wearable device user in a graphical and text format;

l. wherein an alert from a critical situation is sent to the cloud based portal;

m. wherein the alert is received by the cloud based portal and sent to caregivers and family members of the wearable device user;

n. wherein the alert will repeat every predetermined time interval until the alert is cancelled;

o. wherein graphical reports are generated and allow caregivers to see trends and analyze events leading to an incident;

p. wherein data from the wearable device is made available to registered caregivers and family members through computers or mobile devices, and alerts are sent via SMS or e-mail notifications;

q. storing at a non-transitory data storage medium data including one or more selected from the group consisting of a user identification, login credentials, patient-wearable monitoring device data, sensor-captured data, user profiles, data access permissions, notifications/alerts, and reminders;

r. making available the sensor-captured data as well as other data to a caregiver or a doctor in order to look back in time a few hours, a day, a week or a month before an incident;

s. wherein any two or more of the transmitter, the vital signs measurement sensor, and the one or more sensors are configured as part of a System-on-Chip device;

t. wherein multiple patient-wearable monitoring devices connect to the same gateway, so that multiple users utilize the same gateway device if they live together at home, visit each other, or are in the same location, because a single gateway is shared between the devices;

u. wherein the patient-wearable monitoring device being worn is verified by measuring two parameters separately:
  I. a first parameter is from the reflectance heart rate monitor of the vital signs measurement sensor, if no heart beat is detected, the device is likely not being worn;
  II. a second parameter is from the temperature sensor, which should be within a reasonable range of human temperature range, and if not, the device is likely not being worn:

v. wherein if either parameter indicates that the patient-wearable monitoring device is not being worn, alert data is sent to the gateway, the monitoring cycle is terminated to save power, the system-on-chip microprocessor integrated with transmitter and all sensors except the accelerometer are put in sleep mode either for a predetermined time, or until user wearing is detected;

w. wherein the system-on-chip microprocessor integrated with transmitter and the sensors are woken up to obtain readings of vital signs, even if the movement sensor does not detect any motion, every predetermined interval, where the predetermined interval is programmable;

x. wherein self-diagnostics including reading a battery voltage level of the power source and checking if the wearable device is being worn, are performed when the system-on-chip microprocessor integrated with transmitter is woken up;

y. wherein the patient-wearable monitoring device is authenticated and paired to the gateway by bringing it to within a close proximity to the gateway using the transceiver within the system-on-chip microprocessor integrated with transmitter;

z. wherein the gateway device includes electronics hardware and software logic that communicate to the ultra-low power network and the Cloud Computing Services, such that the gateway device is a hub of the ultra-low power network;

aa. wherein the electronics hardware of the gateway device includes a transceiver, a Mic/speaker, a 2-way communication hub, a WAN (wide area network) interface, a plurality of buttons, a NFC/RFID reader to identify wearable device identification, a GPS receiver, a LCD screen, memory and a processor coupled to the aforementioned components;

ab. wherein the gateway device is supplied by a gateway power supply, which is a combination of a rechargeable battery and an external main charger to keep the battery charged while plugged into AC power;

ac. wherein the buttons of the gateway device include hardware and software buttons, and allow a user to clear reminders and alarms, which are programmably set according to user preferences;

ad. wherein the transceiver of the gateway device is a Bluetooth 4.0 and/or 802.15.4 transceivers and communicates to the ULPN;

ae. wherein the WAN interface comprises a cellular transceiver and a Wi-Fi transceiver;

af. wherein the WAN interface couples to the cloud computing server using the Cellular transceiver and/or Wi-Fi transceiver;

ag. wherein the WAN Interface comprises software codes to maintain and prioritize connection to the wide area network;

ah. wherein the gateway device allows 2-way communications with authenticated caregivers via a 2-way communication hub;

ai. wherein the microphone/speaker and the LCD screen are integrated within the gateway device for voice input and voice output to facilitate communications;

aj. wherein the gateway device is either fixed or portable;

ak. wherein the GPS receiver is integrated within the gateway device for tracking the exact location of the gateway device, if the gateway device is portable;

al. wherein the gateway device further comprises modules for administration tasks, to provide security, authentication, data compression and self-diagnosis;

am. wherein the self-diagnostics module monitors and reports hardware, software and networking issues; and an. wherein the gateway device is either a tablet computing device with a custom application or the gateway device is constructed with custom hardware and custom software; and ao. wherein a business intelligence process runs every three hours, or at some other predetermined time interval, to analyze trends and patterns, enabling the provision of proactive and preventive care.

2. A health status monitoring and reporting method of using a health status and monitoring system, comprising:

a. monitoring the health status of a patient using a patient-wearable monitoring device, the patient-wearable monitoring device comprising:

I. a water proof wearable device band, attached to an upper arm of a user;

II. a power source, such that the power source only needs to be recharged after several weeks;

III. a vital signs measurement sensor, which is both a reflectance heart rate monitor and a reflectance oximeter;

IV. wherein the vital signs measurement sensor comprises an Infrared LED, a red LED, a photo sensor, and an analog front end device with operational amplifiers and filters, to obtain heart rate and oxygen saturation level by measuring the light reflected by the user's upper arm, with none of the sensors actually touching the skin;

V. a positional sensor that is a 3-axis gyroscope, a movement sensor that is a 3-axis accelerometer, a pressure sensor, and an digital infrared temperature sensor;

VI. a capacitive proximity detector for determining if the patient-wearable monitoring device is being worn:

VII. an NFC/RFID tag for identification;

VIII. a system-on-chip microprocessor coupled to the vital signs device and either or both of a positional sensor and a movement sensor by either or both of a I2C bus and an SPI bus;

IX. a transmitter coupled with the power source and configured to transmit from the patient-wearable monitoring device to an ultra-low power network (ULPN) data received from one or more of the vital signs measurement sensor, the positional sensor, the movement sensor and the pressure sensor;

X. the transmitter further configured to communicate with the ULPN via either or both of low energy Bluetooth and IEEE 802.15.4 communication protocols;

XI. the transmitter further configured as a wireless signal transceiver and integrated with the system-on-chip microprocessor;

b. a gateway device coupled to the ULPN to transmit the data from the ULPN to a Wide Area Network (WAN);

c. the gateway device configured to transmit the data to the WAN via at least one of cellular and Wi-Fi communication technologies;

d. wherein the movement sensor detects critical situations, and if so detected, generates an interrupt to wake up the System-on-Chip microprocessor to perform further analysis, and to send the data and an alert to the gateway device using the ultra-low power network;

e. the critical situations that the movement sensor can detect consist of the user tapping on the wearable device, which indicates a request for help in the manner of a panic button;

f. the movement sensor also detects motion;

g. the movement sensor is the only part of the wearable device that is always on, and can conserve power by being the only part of the wearable device that is on;

h. wherein environmental sensors

I. detect opening and closing of doors,

II. detect ambient light and temperature,

III. detect sound,

IV. detect motion,

V. read Near Field Communications (NFC) tags for identification of the user of the patient-wearable monitoring device and tracking the location of the user of the patient-wearable monitoring device, and VI. read Radio Frequency Identification (RFID) tags for identification of the user of the patient-wearable monitoring device and tracking the location of the user of the patient-wearable monitoring device;

i. storing at a non-transitory data storage medium data including a unique identification corresponding to the patient-wearable monitoring device;

j. wherein the gateway device transmits data from the ULPN to a cloud based portal for processing, data storage, or notifications;

k. wherein the cloud based portal analyzes the collected data and displays results on a dashboard;

l. wherein the cloud based portal is accessible to registered caregivers and family members of the wearable device user in a graphical and text format;

m. wherein an alert from a critical situation is sent to the cloud based portal;

n. wherein the alert is received by the cloud based portal and sent to caregivers and family members of the wearable device user;

o. wherein the alert will repeat every predetermined time interval until the alert is cancelled;

p. wherein graphical reports are generated and allow caregivers to see trends and analyze events leading to an incident;

q. wherein data from the wearable device is made available to registered caregivers and family members through computers or mobile devices, and alerts are sent via SMS or e-mail notifications;

r. storing at a non-transitory data storage medium data including one or more selected from the group consisting of a user identification, login credentials, patient-wearable monitoring device data, sensor-captured data, user profiles, data access permissions, notifications/alerts, and reminders;

s. making available the sensor-captured data as well as other data to a caregiver or a doctor in order to look back in time a few hours, a day, a week or a month before an incident;

t. wherein any two or more of the transmitter, the vital signs measurement sensor, and the one or more sensors are configured as part of a System-on-Chip device;

u. wherein multiple patient-wearable monitoring devices connect to the same gateway, so that multiple users utilize the same gateway device if they live together at home, visit each other, or are in the same location, because a single gateway is shared between the devices;

v. wherein the patient-wearable monitoring device being worn is verified by measuring two parameters separately:
   I. a first parameter is from the reflectance heart rate monitor of the vital signs measurement sensor, if no heart beat is detected, the device is likely not being worn;
   II. a second parameter is from the temperature sensor, which should be within a reasonable range of human temperature range, and if not, the device is likely not being worn;

w. wherein if either parameter indicates that the patient-wearable monitoring device is not being worn, alert data is sent to the gateway, the monitoring cycle is terminated to save power, the system-on-chip microprocessor integrated with transmitter and all sensors except the accelerometer are put in sleep mode either for a predetermined time, or until user wearing is detected;

x. wherein the system-on-chip microprocessor integrated with transmitter and the sensors are woken up to obtain readings of vital signs, even if the movement sensor does not detect any motion, every predetermined interval, where the predetermined interval is programmable;

y. wherein self-diagnostics including reading a battery voltage level of the power source and checking if the wearable device is being worn, are performed when the system-on-chip microprocessor integrated with transmitter is woken up;

z. wherein the patient-wearable monitoring device is authenticated and paired to the gateway by bringing it to within a close proximity to the gateway using the transceiver within the system-on-chip microprocessor integrated with transmitter;

aa. wherein the gateway device includes electronics hardware and software logic that communicate to the ultra-low power network and the Cloud Computing Services, such that the gateway device is a hub of the ultra-low power network;

ab. wherein the electronics hardware of the gateway device includes a transceiver, a Mic/speaker, a 2-way communication hub, a WAN (wide area network) interface, a plurality of buttons, a NFC/RFID reader to identify wearable device identification, a GPS receiver, a LCD screen, memory and a processor coupled to the aforementioned components;

ac. wherein the gateway device is supplied by a gateway power supply, which is a combination of a rechargeable battery and an external main charger to keep the battery charged while plugged into AC power;

ad. wherein the buttons of the gateway device include hardware and software buttons, and allow a user to clear reminders and alarms, which are programmably set according to user preferences;

ae. wherein the transceiver of the gateway device is a Bluetooth 4.0 and/or 802.15.4 transceivers and communicates to the ULPN;

af. wherein the WAN interface comprises a cellular transceiver and a Wi-Fi transceiver;

ag. wherein the WAN interface couples to the cloud computing server using the Cellular transceiver and/or Wi-Fi transceiver;

ah. wherein the WAN Interface comprises software codes to maintain and prioritize connection to the wide area network;

ai. wherein the gateway device allows 2-way communications with authenticated caregivers via a 2-way communication hub;

aj. wherein the microphone/speaker and the LCD screen are integrated within the gateway device for voice input and voice output to facilitate communications;

ak. wherein the gateway device is either fixed or portable;

al. wherein the GPS receiver is integrated within the gateway device for tracking the exact location of the gateway device, if the gateway device is portable;

am. wherein the gateway device further comprises modules for administration tasks, to provide security, authentication, data compression and self-diagnosis;

an. wherein the self-diagnostics module monitors and reports hardware, software and networking issues; and ao. wherein the gateway device is either a tablet computing device with a custom application or the gateway device is constructed with custom hardware and custom software; and ap. wherein a business intelligence process runs every three hours, or at some other predetermined time interval, to analyze trends and patterns, enabling the provision of proactive and preventive care.

* * * * *